United States Patent [19]

Költringer

[11] Patent Number: 5,118,505
[45] Date of Patent: Jun. 2, 1992

[54] COMBINATION PREPARATION FOR THE TREATMENT OF NERVE CELL AND NERVE FIBRE DISEASES AND INJURY

[76] Inventor: Peter Költringer, Lortzinggasse 20, A-8041 Graz, Austria, 8041

[21] Appl. No.: 301,424

[22] Filed: Jan. 25, 1989

[30] Foreign Application Priority Data

| Jan. 28, 1988 | [DE] | Fed. Rep. of Germany | 3802567 |
| Feb. 1, 1988 | [DE] | Fed. Rep. of Germany | 3802895 |
| Apr. 21, 1988 | [DE] | Fed. Rep. of Germany | 3813451 |

[51] Int. Cl.$^5$ ................ A61K 35/78; A61K 31/70; A61K 31/505
[52] U.S. Cl. .................. 424/195.1; 514/25; 514/52; 514/260; 514/276; 514/560
[58] Field of Search ........ 424/195.1; 514/25, 52, 514/251, 260, 276, 560

[56] References Cited

U.S. PATENT DOCUMENTS

| 4,571,407 | 2/1986 | Chatterjee et al. | 514/464 |
| 4,753,929 | 6/1988 | Matsumoto et al. | 514/27 |
| 4,938,960 | 7/1990 | Ismail | 424/195.1 |

OTHER PUBLICATIONS

Chem. Abst., 104:45706s, 1986.
Chem. Abst., 107:205183m, 1987.
Chem. Abst., 103:76258f, 1985.

*Primary Examiner*—John W. Rollins
*Attorney, Agent, or Firm*—Townsend and Townsend

[57] ABSTRACT

The invention relates to a combination preparation, in particular for the treatment of nerve cell and nerve fibre diseases and also for the prophylaxis and treatment of circulatory disturbances, the combination preparation comprising at least the active substances Extr. Ginkgo bilobae (ginkgo flavonglycosides) and at least one substance of the group: folic acid and its derivatives, in particular folinic acid; α-lipoic acid and its derivatives; and all the vitamin-B groups and their derivatives. Investigations have been successfully carried out in the treatment of diabetes mellitus, hyperpathic polyneuropathy and carpal tunnel syndrome.

21 Claims, No Drawings

COMBINATION PREPARATION FOR THE TREATMENT OF NERVE CELL AND NERVE FIBRE DISEASES AND INJURY

The present invention relates to a combination preparation, in particular for the treatment of nerve cell and nerve fibre diseases and of circulatory disturbances, and also for the prophylaxis of circulatory disturbances.

Such nerve cell and nerve fibre diseases include various indications, for example
  a) all neuropathic diseases,
  b) degenerative nerve fibre and nerve cell processes in the peripheral and central nervous system,
  c) all neuralgia of the most diverse genesis,
  d) viral and bacterial infections which attack nerve fibres and nerve cells, for example herpes, in particular herpes zoster.

Furthermore, the preparation is suitable for nerve cell and nerve fibre regeneration after injury to the latter, and indeed for nerve fibres of all qualities, i.e. both motoric and also sensory and also vegetative.

Many of the above recited diseases are associated with extreme and unpleasant pain and can presently only be poorly treated if at all. Moreover, in cases where a certain degree of relief is possible it is frequently necessary to use medications which have undesired counter-indications.

The object of the present invention is to provide assistance here and to provide a combination preparation which, with the abovementioned diseases and injuries, brings about a substantial relief from pain and/or a regeneration of the affected nerve cells and nerve fibres, and which is optionally also useful for the treatment and prophylaxis of circulatory disturbances.

In order to satisfy this object the present invention provides a combination preparation which comprises at least the active substances Extr. Ginkgo bilobae (ginkgo flavonglycosides) and at least one substance of the group: folic acid and its derivatives, in particular folinic acid; α-lipoic acid and its derivatives; and all the vitamin-B groups and their derivatives.

Extr. Ginkgo bilobae which comprises ginkgo flavonglycosides is a pure plant extract which is obtainable commercially under the trademark Tebonin (registered trademark of the company Dr. Willmar Schwabe, Karlsruhe). An ampoule of this product to 5 ml contains: Extr. Ginkgo bilobae e fol.sicc. puriss. pro inject. 17.5 mg stand. to 4.2 mg ginkgo flavonglycosides. Tebonin has previously been successfully used in practice for the treatment of circulatory disturbances.

In the treatment of diabetic patients with nerve degeneration, i.e. in the treatment of patients with polyneuropathy, it has surprisingly been shown that the treatment with Tebonin in combination with folic acid or with α-lipoic acid has led to an extensive relief from pain and to substantial improvement. This is particularly astonishing since folic acid and α-lipoic acid are normally not used with diabetic patients but are rather used as an antidote of the folic acid antagonist methotrexate used in tumor chemotherapy, and for the treatment of hepatitis and acute heavy metal poisoning.

As a result of the clinical investigations which have been carried out so far there are indications that the combination preparation of the invention can be used for the treatment of all the above designated diseases and injuries. Furthermore it is assumed, as a result of the related structures, that the effect which is achieved can also be achieved with derivatives of folic acid and of α-lipoic acid and also with the named vitamins of the vitamin B-group.

Furthermore, it has surprisingly been found that the preparation of the invention enables a substantially improved treatment of circulatory disturbances and is also suitable for the prophylaxis of circulatory disturbances, at least in the form of a combination of the active substances Extr. ginkgobilobae (ginkgo flavonglycosides) and one or more substances of the group folic acid and its derivatives; in particular folinic acid. Initial clinical investigations have shown that whereas Tebonin on its own brings about a good reduction of the viscoelasticity of the blood, but does not bring about the reduced thrombocyte aggregation which is desired in its own right, the combination preparation brings about a substantial further reduction in viscoelasticity, and also a massive reduction of the thrombocyte aggregation. It is therefore to be assumed that the combination preparation will prove to be very effective as a preventive measure against heart attacks amongst other things. The enormous significance of the new combination preparation will become clear if one takes account that the previous prevention of circulatory disturbances leading to heart attacks has taken place with preparations containing aspirin, with the taking of this preparation leading to disturbing side effects, whereas the combination preparation of the invention has to date shown no undesired side effects. It should be briefly mentioned at this juncture that neither folic acid nor folinic acid on its own has produced a reduction of the viscosity of the blood or a lowering of the thrombocyte aggregation. In the comparison tests which have been employed the thrombocyte aggregation has been evaluated in accordance with four different criteria and indeed spontaneously, after the addition of adenosine diphosphate, after the addition of ephinephrine and after the addition of collagen, and that the above recited judgement concerning the measurement of the thrombocyte aggregation was confirmed in accordance with all four criteria.

Particularly effective combinations and ranges for the daily doses to be used are to be found in the subordinate claims.

The invention will be explained in more detail in the following with reference to examples.

EXAMPLE 1

An infusion solution for a daily dosage was prepared, and indeed from 250 ml physiological kitchen salt solution with 25 ml Tebonin and a 1 ml ampoule of calcium folinate from the company Ebewe, which contained 3.24 mg calcium folinate (anhydrous) corresponding to 3 mg folinic acid in aqueous solution.

Three patients with diabetes mellitus and hyperpathic polyneuropathy were then treated with this solution. After only three days a substantial improvement was found in all patients. The treatment was continued in all cases until the patients were free of pain. In the most favourable case this already occurred with one patient after four days. With the other patients on the 11th and 14th day respectively. Thereafter the treatment was terminated. The duration of the infusions was between 1 and 2 hours per day for all patients. More than three months after this treatment no repetition of the symptoms could be found in any of the patients.

Measurements of the speed of conduction of the nerves have shown that this had already improved by 20 to 30% after 4 to 8 days treatment.

EXAMPLE 2

Infusion solutions were also prepared in this case, with a daily dosage consisting of 250 mg physiological kitchen salt solution, 25 ml of Tebonin and two Tioctan ampoules with each ampule containing 5 ml (equal to 50 mg of α-lipoic acid (6.8-dithiooctanic acid). Two further patients with diabetes mellitus and hyperpathic polyneuropathy were treated with this solution. Once again the infusion took place once daily with an infusion duration between 1 and 2 hours.

In this case also a substantial improvement took place after a few days and the treatment was so successful that it could be terminated after 10 and 14 days respectively. Moreover, after more than one month since this treatment, no repetition of the symptoms had occurred.

In all patients who were treated in accordance with examples 1 and 2 the hyperpathy disappeared. A clinical investigation of the depth of sensitivity was carried out with one patient and the result of this investigation confirmed the success which had been achieved. Incompatibility reactions were not found in any of the patients who were investigated.

EXAMPLE 3—CONTROL EXAMPLE

Further patients with diabetes mellitus and hyperpathic polyneuropathy were treated with infusion solutions with the solution again consisting of physiological kitchen salt solution 250 ml, but provided in each case with only one of the named active ingredients, i.e. Tebonin, folinic acid and α-lipoic acid.

In the patients who were treated with the Tebonin solution alone the duration of the treatment extended over 14 days without any improvement of the condition occurring at all. With patients who were treated with folinic acid alone no improvement could be found after 14 days. Patients who were treated with α-lipoic acid solution were indeed treated for up to three weeks without any notible effect occurring.

EXAMPLE 4

A patient with carpal tunnel syndrome was treated with the infusion solution in accordance with example 1. After treatment for one week a substantial recession of the malady was found with this patient. The treatment is presently being continued and the condition of the patient is improving from day to day.

EXAMPLE 5

Since the combination preparation had proved very effective in treating nerve cell and nerve fibre diseases an investigation was carried out with two patients whether the preparation would bring about an improved benefit in treating circulatory disturbances when compared with treatment with Tebonin on its own. In this investigation it was found that the combination preparation led to a reduction of the viscosity and an improvement in the aggregation characteristics of the blood of the patients, with this change persisting longer and being achieved with lower doses than on treatment with Tebonin on its own. As a result of these initial results one assumes that the combination preparation is well suited for the treatment of all circulatory disturbances both peripheral and also central circulatory disturbances.

EXAMPLE 6

In order to substantiate the presumption expressed at the end of example 5 and to determine whether prevention of circulatory disturbances would be possible 10 volutary healthy patients, some male and some female in the age from 20 to 40 years were treated daily over a period of 10 days with the combination preparation. In this case the combination preparation was administered in pill form, with each patient taking once daily two tablets of Tebonin (each tablet contained: dried extract of ginkgo-biloba leaves (50:1) 40 mg adjusted to 9.6 mg ginkgo flavonglycosides) and one tablet Folsan (registered trademark) which contain 5 mg folic acid (active constituent folinic acid).

For control purposes further patients were treated with Tebonin along and yet further patients with folic acid alone. Blood samples of the patients were then investigated with respect to the viscoelasticity and the thrombocyte aggregation. For the investigation of the thrombocyte aggregation a part of the blood samples that were taken was split into four samples and these four samples were respectively investigated in accordance with the four customary criteria of thrombocyte aggregation, i.e. spontaneous, after the addition of adenosine diphosphate, after the addition of ephinephrine and after the addition of collagen respectively.

After statistical evaluation it was found that in comparison to Tebonin on its own the treatment with the combination preparation of the invention achieved a substantial further reduction of the viscoelasticity and also a massive reduction of the thrombocyte aggregation. It is known that Tebonin on its own is not able to reduce thrombocyte aggregation. Folic acid brings about neither a reduction of the viscoelasticity nor a lowering of the thrombocyte aggregation of the blood.

In the course of this investigation it was also found that after peroral administration of four Tebonin tablets and one Folsan tablet a substantial improvement of the viscoelasticity and also of the thrombocyte aggregation was achieved after three hours. Thus a treatment of this kind is suitable as an immediate measure following a heart attack.

It should be mentioned that α-lipoic acid is also known as thioct acid.

I claim:

1. A pharmaceutical composition for the treatment or prophylaxis of nerve cell and nerve fiber diseases and of circulatory disturbances, the composition comprising an effective amount of active substances comprising Ginkgo bilobae extract (ginkgo flavonglycosides) and at least one substance of the group: folic acid and its derivatives; α-lipoic acid (thioct acid) and its derivatives; and all the vitamin-B groups and their derivatives.

2. A composition in accordance with claim 1, wherein the Ginkgo bilobae extract is TEBONIN Ginkgo bilobae extract and the folic acid derivative is folinic acid.

3. A composition in accordance with claim 2, wherein the active substances are in a daily dosage form comprising 5–100 ml TEBONIN Ginkgo bilobae extract and 1 to 15 mg folinic acid.

4. A composition in accordance with claim 3 wherein the daily dosage form comprises 20 to 35 ml TEBONIN Ginkgo bilobae extract and 2 to 4 mg folinic acid.

5. A composition in accordance with claim 4 wherein the daily dosage form comprises 25 ml TEBONIN Ginkgo bilobae extract and 3 mg folinic acid.

6. A composition in accordance with claim 1, wherein the active substances comprise α-lipoic acid and the Ginkgo bilobae extract is TEBONIN Gingko bilobae extract.

7. A composition in accordance with claim 6, wherein the active substances are in a daily dosage form comprising 5-100 ml TEBONIN Ginkgo bilobae extract and 25 to 400 mg α-lipoic acid.

8. A composition in accordance with claim 7 wherein the daily form comprises 20 to 30 ml TEBONIN Ginkgo bilobae extract and 40 to 150 mg α-lipoic acid.

9. A composition in accordance with claim 8 wherein the daily dosage form comprises 25 ml TEBONIN Ginkgo bilobae extract and 100 mg α-lipoic acid.

10. A composition in accordance with claim 1, wherein the active substances comprise at least one of the group consisting of vitamins $B_1$, $B_2$, $B_6$, $B_{12}$ and a B-complex and the Ginkgo bilobae extract is TEBONIN Ginkgo bilobae extract.

11. A composition in accordance with claim 10, wherein the active substances are in a daily dosage form comprising 5 to 100 ml TEBONIN Ginkgo bilobae extract and 0.1 to 0.4 mg of crystalline vitamin $B_1$ (aneurin).

12. A composition in accordance with claim 10, wherein the active substances are in a daily dosage form comprising 5 to 100 ml TEBONIN Ginkgo bilobae extract and 10 to 50 mg vitamin $B_2$ (lactoflavin).

13. A composition in accordance with claim 10, wherein the active substances are in a daily dosage form comprising 5 to 100 ml TEBONIN Ginkgo bilobae extract and 20 to 250 mg vitamin $B_6$ (pyridoxin-hydrochloride).

14. A composition in accordance with claim 10, wherein the active substances are in a daily dosage comprising 5 to 100 ml TEBONIN Ginkgo bilobae extract and 0.2 to 10 mg vitamin $B_{12}$ (cyanocobalamin).

15. A composition in accordance with claim 1, wherein the active substances are present in pill form, liquid form or powder form for peroral administration.

16. A composition in accordance with claim 4 further comprising 0.5 to 4 mg pyridoxin.

17. A composition in accordance with claim 10, wherein the active substances are in a daily dosage form comprising 5 to 100 ml TEBONIN Ginkgo bilobae extract and vitamin B-complex with aneurin 5 to 20 mg, lactoflavin 1 to 4 mg, nicotinic amide 10 to 50 mg, adermin 1 to 9 mg and pantothenic acid salts of calcium 2 to 20 mg.

18. A composition in accordance with claim 1, further comprising 250 ml of a physiological kitchen salt solution.

19. A composition in accordance with claim 1, wherein the active substances are present in powder form, pills, liquid form, ampoules, or as an ointment for treating open wounds.

20. A composition in accordance with claim 15 wherein the daily dosage form comprises ginkgo-biloba leaves (50:1) 80 to 120 mg adjusted to 19.2-28.8 mg ginkgo flavonglycosides and 3-8 mg folic acid.

21. A composition in accordance with claim 15, for the prophylaxis of circulatory disturbances wherein the active substances are in a daily dosage form comprising dried extract of ginkgo-biloba leaves (50:1) 40 to 160 mg adjusted to 9.6-38.4 mg ginkgo flavonglycosides and 1-15 mg folic acid.

* * * * *